United States Patent [19]

Chang et al.

[11] Patent Number: 4,863,636

[45] Date of Patent: Sep. 5, 1989

[54] SUBSTITUTED N-HYDROXYPHTHALIMIDES AND THEIR USE AS DETERGENT ADDITIVES

[75] Inventors: Laurence W. Chang, Orange, Conn.; Robert G. Fischer, Stevensville, Canada

[73] Assignee: American Cyanamid Company, Stamford, Conn.

[21] Appl. No.: 156,131

[22] Filed: Feb. 12, 1988

[51] Int. Cl.[4] ...................... C11D 3/28; C07D 209/48

[52] U.S. Cl. .................................. 252/542; 252/544; 252/545; 252/546; 548/473; 548/475; 560/37; 562/450; 562/430

[58] Field of Search .................. 548/473, 475; 560/37; 562/450, 430; 252/542, 544, 545, 546

[56] References Cited

U.S. PATENT DOCUMENTS 3,767,671 10/1973 Klebe et al. ......................... 548/473

3,915,879 10/1975 Barnett et al. ....................... 560/37

*Primary Examiner*—Paul Lieberman

*Assistant Examiner*—Christine A. Skane

*Attorney, Agent, or Firm*—Steven H. Flynn

[57] ABSTRACT

N-hydroxyimide compounds derived from substituted phthalic anhydride are provided which exhibit strong metal ion chelating ability, making them useful as detergent additives, in boiler water systems, as reaction intermediates, etc. A detergent composition containing N-hydroxyimide and/or carboxy hydroxamic acid detergent additives is also disclosed.

9 Claims, No Drawings

SUBSTITUTED N-HYDROXYPHTHALIMIDES AND THEIR USE AS DETERGENT ADDITIVES

The present invention relates to chelating agents which are useful as adjuvants for detergents and to detergent compositions, particularly fabric-washing detergent compositions. In particular it relates to novel N-hydroxyimide compounds having good transition metal ion chelating properties and to detergent compositions comprising at least one detersive surfactant and an effective amount of an N-hydroxyimide detergent additive.

BACKGROUND OF THE INVENTION

Detergent compositions have long employed materials, known as "builders", to improve the detergency of soaps and synthetic detergents by actively chelating alkali metal cations which are normal components of "hard" tap water. Such builders have been found to affect, for instance, soil suspension, emulsification of soil particles, solubilization of water-insolubles, and inactivation of various mineral constitutents present in a detergent system. Many materials useful as builders have been proposed, and their effects are known. See, e.g., U.S. Pat. Nos. 3,852,213, 3,950,260, 4,182,718, and 4,440,646 (all incorporated herein by reference).

Recently, however, the attention of detergent manufacturers and researchers has turned.to the role of heavier metal cations, i.e., transition metal cations, in the formation of stain complexes on fabrics and other surfaces. It has been observed that these multivalent transition metal cations, particularly iron ($Fe^{+++}$, enhance the binding of the components of many stains to substrates, and breaking up the cation-enhanced bonds is an effective approach to stain removal. Therefore, there is a strong need for the discovery of new materials that are effective as chelating agents for transition metal cations, are easy to prepare, and can be added to detergent compositions in economical amounts to boost stain-removing power.

It has now been discovered that certain cyclic N-hydroxyimide compounds derived from substituted phthalic anhydride are active metal ion chelants and are useful as detergent additives. The N-hydroxyphthalimides of the present invention are water-soluble and form soluble chelates with transition metal ions which hinder detergent action and form stain complexes on fabrics and other substrates. In basic solutions, e.g., above about pH 9, ring-opened derivatives of the N-hydroxyphthalimides are believed to be produced, yielding carboxy hydroxamic acid-functional derivatives which are active metal ion chelants as well.

SUMMARY OF THE INVENTION

It is therefore an object of the present invention to provide a new class of metal ion chelating agents.

It is a further object of the present invention to provide new detergent additives which are active in stain removal.

It is a further object of the present invention to provide a detergent additive free of phosphorus.

It is a further object of the present invention to provide a novel detergent composition.

It is a further object of the present invention to provide a fabric-washing detergent composition that is effective in stain removal.

These and other objects are achieved, according to the present invention, by compounds having the formula

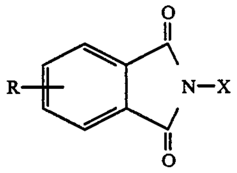

(I)

wherein R is carboxy, sulfo, or caroxyalkyl or sulfonalkyl having 1-12 carbon atoms, or alkali metal salts thereof; and X is hydroxy or $—O^-M^+$, where $M^+$ is an alkali metal cation (i.e., $Li^+$, $Na^+$, $K^+$, etc.).

Also contemplated are ring-opened derivatives of the the Formula I compounds, which have the formula

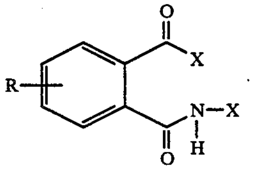

(II)

wherein X and R are as defined above.

Also contemplated herein are detergent compositions comprising one or more detersive surfactants and one or more detergent additives consisting essentially of N-hydroxyphthalimide compounds having the formula

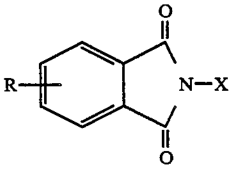

or

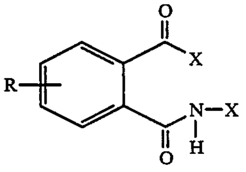

where X and R are as defined above.

DETAILED DESCRIPTION OF THE INVENTION

The N-hydroxyimide detergent additives of the present invention are advantageously prepared by reacting a substituted phthalic anhydride with hydroxylamine or a salt thereof to obtain the N-hydroxyimides of the present invention. The substituted N-hydroxyimide compounds may be further reacted in the presence of base to obtain ring-opened substituted mono-hydroxamated phthalic acid. Thus, a typical reaction scheme for the preparation of detergent additives according to the present invention is as follows:

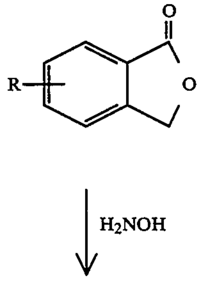

substituted phthalic anhydride hydroxylamine

-continued

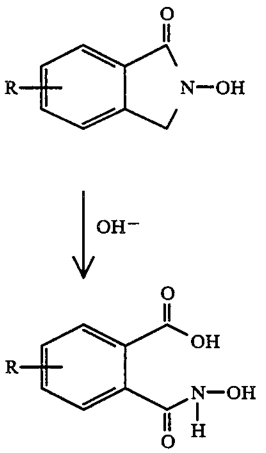

substituted N—hydroxyphthalimide substituted monohydroxamated phthalic acid

Phthalic anhydride is a well-known intermediate in the manufacture of, e.g., inks and synthetic resins. Many substituted phthalic anhydrides suitable for use in the present invention are also known. Carboxy-substituted phthalic anhydride, e.g., 1,3-dioxo-5-phthalancarboxylic acid ("trimellitic anhydride"), is a well-known intermediate in the preparation of resins, adhesives, polymers, dyes and printing inks. The substituted phthalic anhydride compounds suitable for use in preparing the N-hydroxyphthalimide compounds of the present invention will have terminal carboxylic acid or sulfonic acid groups bonded directly or by a $C_1$–$C_{12}$ alkylene bridging group to the benzene ring of the phthalic anhydride moiety. Carboxy-substituted phthalic anhydride and sulfo-substituted phthalic anhydride are preferred.

Reaction of the substituted phthalic anhydride to obtain N-hydroxyimide products may be accomplished by contacting the substituted phthalic anhydride with at least an equimolar quantity of hydroxylamine or a salt thereof, preferably hydroxylamine hydrochloride. The reaction will normally be carried out in the presence of about 2–5 moles per mole of hydroxylamine of a basic agent, preferably an organic base such as sodium methoxide, sodium ethoxide, sodium acetate, pyridine, triethylamine, or quinoline. Most preferably, the reaction will be carried out in an alcoholic solvent, such as methanol or ethanol.

The product may be isolated in any one of a number of known ways. For example, the product can be isolated by precipitation from a non-solvent, such as hexane, and the precipitate filtered, washed and dried under vacuum to give the N-hydroxyimide product.

Alternatively, flash or spray drying may be used. The drying step removes substantially all of the organic base, and washing with alcoholic hydrogen chloride effectively scavenges residual amounts, in cases where complete removal of the basic agent is required.

In basic solution, as discussed previously, it is believed that the N-hydroxyphthalimides of the present invention undergo a ring-opening reaction to at least some degree. Therefore, detergent additives according to this invention may comprise substituted N-hydroxyphthalimides (unopened form) and substituted monohydroxamated phthalic acid moieties (opened form), as seen in Formulas I and II, supra. Alkali metal salts, especially sodium salts, of the substituted N-hydroxyphthalimides and their carboxy hydroxamic acid derivatives are also contemplated. The multiple functionality of the N-hydroxyimide and carboxy hydroxamic acid compounds, and the variety of spacings possible (from molecule to molecule) between the functional groups, may enhance the metal chelating effectiveness of the compounds by allowing them to sequester a wider variety of cations.

The N-hydroxyimide compounds and derivatives are active stain removers and are advantageously included in a detergent composition, in accordance with the present invention. A detergent composition of this invention will contain at least one detersive surfactant. Such surfactants will be present in amounts usually encountered in detergent compositions, e.g., from about 1 to about 50% by weight, preferably about 5 to about 25% by weight for fabric-washing detergents, and most preferably from about 10 to about 20% by weight based on the total weight of the detergent composition. The surfactants may be anionic, nonionic, cationic or amphoteric, and mixtures of different detersive surfactants may be used. Non-limiting examples of suitable detersive surfactants include:

(a) Anionic surfactants: soaps, i.e., alkali metal (preferably sodium or potassium) salts of long-chain fatty acids containing from 8 to 20 carbon atoms, such as lauric, myristic, oleic, palmitic, capric, caprylic, and stearic acids, used singly or in mixtures of differing chain lengths; alkali metal salts of organic sulfuric reaction products having long hydrocarbon chains of about 8 to about 20 carbon atoms and a radical selected from the group consisting of sulphonic acid and sulfuric acid ester radicals, such as sodium or potassium alkyl sulphates, preferably those obtained by sulphating higher ($C_8$–$C_8$) alcohols; sodium or potassium alkyl benzenesulphonates in which the alkyl group contains from about 9 to about 20 carbon atoms, such as sodium linear alkyl ($C_{10}$–$C_{15}$) secondary benzenesulphonate, 2-phenyl-dodecanesulphonate, 2-phenyl-octadecanesulphonate and 3-phenyl-dodecanesulphonate; alkali metal (preferably sodium) olefin sulphonates, i.e., the mixture of detersive surfactants obtained from sulphonation of $C_8$–$C_{22}$ olefins, preferably straight-chain alpha-olefins; sodium alkyl glyceryl ether sulphonates, including ethers of higher alcohols derived from tallow coconut oil and synthetic alcohols derived from petroleum; sodium coconut oil fatty acid monoglyceride sulphates and sulphonates; sodium or potassium salts of sulfur acid esters of the reaction between higher fatty alcohols (e.g., tallow or coconut oil alcohols) and ethylene oxide; the esterification products of fatty acids with isethionic acid, neutralized with sodium hydroxide; and sodium or potassium salts of fatty acid amides of methyl taurine.

(b) Nonionic synthetic detersive surfactants: compounds formed by condensing ethylene oxide with a hydrophobic base formed by the condensation of propylene oxide with propylene glycol; the polyethylene oxide condensates of alkyl-phenols, e.g., the condensation products of alkyl-phenols, having an alkyl group containing from about 6 to 12 carbon atoms in either a straight or branched chain, with ethylene oxide, said ethylene oxide being present in amounts equal to 5 to 25 moles of ethylene oxide per mole of alkyl-phenols (the alkyl substituent in such compounds may be derived from polymerised propylene, diisobutylene, octene dodecene, or nonene, for example); compounds derived from the condensation of ethylene oxide with the product resulting from the reaction of propylene oxide and ethylenediamine, such as compounds containing from about 40% to about 80% polyoxyethylene by weight and having a molecular weight of from about 5,000 to about 11,000 resulting from the reaction of ethylene oxide groups with a hydrophobic base constituted of the reaction product of ethylenediamine and excess propylene oxide, said hydrophobic base having a molecular weight of the order of 2,500 to 3,000; the condensation product of aliphatic alcohols having from 8 to 18 carbon atoms, in either straight chain or branched chain configuration, with ethylene oxide, e.g., a coconut alcohol-ethylene oxide condensate having from 6 to 30 moles of ethylene oxide per mole of coconut alcohol, the coconut alcohol fraction having from 10 to 14 carbon atoms; long chain tertiary amine oxides corresponding to the following general formula, wherein $R^1R^2R^3N{=}O$, wherein $R^1$ is an alkyl radical of from about 8 to 18 carbon atoms and $R^2$ and $R^3$ are each methyl, ethyl or hydroxyethyl radicals, such as dimethyldodecylamine oxide, dimethyloctylamine oxide, dimethyldecylamine oxide, diethyltetradecylamine oxide and dimethylhexadecylamine oxide, N-bis (hydroxyethyl)dodecylamine oxide; long chain tertiary phosphine oxides corresponding to the following formula $R^4R^5R^6P{=}O$, wherein $R^4$ is an alkyl, alkenyl, or monohydroxyalkyl radical of 10 to 18 carbon atoms and $R^5$and $R^6$ are each alkyl or monohydroxyalkyl groups containing from 1 to 3 carbon atoms, such as dimethyldodecylphosphine oxide, dimethyltetradecylphosphine oxide, ethylmethyltetradecylphosphine oxide, cetyldimethylphosphine oxide, dimethylstearylphosphine oxide, cetylethylpropylphosphine oxide, diethyldodecylphosphine oxide, diethyltetradecylphosphine oxide, bis(hydroxymethyl)dodecylphosphine oxide, bis(2-hydroxyethyl)dodecylphosphine oxide, 2-hydroxypropylmethyltetradecylphosphine oxide, dimethyloleylphosphine oxide, and dimethyl-2-hydroxydodecylphosphine oxide; and dialkyl sulphoxides corresponding to the following formula, $R^7R^8S{=}0$, wherein $R^7$ is an alkyl, alkenyl, beta- or gamma-monohydroxyalkyl radical or an alkyl or beta- or gamma-monohydroxyoxyalkyl radical containing one or two other oxygen atoms in the chain, the $R^7$ groups ranging from 10 to 18 carbon atoms in chain length, and wherein $R^8$ is methyl, ethyl or alkylol, such as dodecyl methyl sulphoxide, tetradecyl methyl sulphoxide, 3-hydroxytridecyl methyl sulphoxide, 2-hydroxydodecyl methyl sulphoxide, 3-hydroxy-4-decyloxybutyl methyl sulphoxide, 3-hydroxy-4-dodecyloxybutyl methyl sulphoxide, 2-hydroxy-3-decyloxypropyl methyl sulphoxide, 2-hydroxy-3-dodecyloxypropyl methyl sulphoxide, dodecyl ethyl sulphoxide, 2-hydroxydodecyl ethyl sulphoxide, dodecyl-2-hydroxy ethyl sulphoxide.

(c) Ampholytic synthetic surfactants: derivatives of aliphatic secondary and tertiary amines, in which the aliphatic radical may be straight chain or branched chain and wherein one of the aliphatic substituents contains from about 8 to 18 carbon atoms and one contains an anionic water solubilizing group, such as sodium-3-dodecylaminopropionate, sodium3-dodecylaminopropanesulphonate and sodium N-2-hydroxydodecy-N-methyl-taurate.

(d) Zwitterionic synthetic surfactants:

derivatives of aliphatic quaternary ammonium compounds, sulphonium compounds and phosphonium compounds in which the aliphatic radical may be straight or branched chain and wherein one of the aliphatic substituents contains from about 8 to 18 carbon atoms and one contains an anionic water solubilizing group, such as 3-(N,N-dimethyl-N-hexadecylammonio)propane-1-sulphonate, 3-(N,N-dimethyl-N-hexadecylammonio)-2-hydroxypropane-1-sulphonate, 3-(dodecylmethylsulphonium) propane sulphonate, and 3-(cetylmethylphosphonium) ethane sulphonate.

The detergent compositions of the present invention will contain, besides one or more detersive surfactants, about 3% to about 12% by weight of the composition, preferably about 6% by weight, of the N-hydroxyimide and/or the carboxy hydroxamic acid detergent additives described above.

In addition to the surfactants and the N-hydroxyimide and/or carboxy hydroxamic acid compounds, the detergent composition according to the invention may also contain conventional detergent builders such as condensed phosphates, trisodium nitrilotriacetate (NTA), sodium carbonate, zeolites, sodium silicates, etc., and organic polymers such as polyacrylates, polymethacrylates, and polymaleates. See, e.g., U.S. Pat. Nos. 3,392,150, 3,666,664, 3,707,502, 3,839,215 and U.S. Pat. No. 4,067,816, all of which are incorporated herein by reference. -The combined detergent builders will make up from about 10% to about 50% by weight of the detergent composition, preferably about 20% to 40% by weight.

In addition to the essential detersive surfactants and detergent additives, a detergent composition of the invention may comprise such conventional ingredients as lather boosters (e.g., alkanolamides), fillers, antiredeposition agents, fluorescers, pigments, germicides, scents, and enzymes.

A detergent composition according to the invention can be prepared by any conventional manufacturing technique used for preparing detergent compositions, such as slurry making and spray-drying, and the detergent can take anyone of the common physical forms associated with detergents, such as powders, flakes, granules, noodles, cakes, bars and liquids.

Liquid detergent compositions according to the invention will most preferably be concentrated aqueous solutions having a basic pH, at least about pH 9, comprising one or more of the detersive surfactants described above and one or more of the N-hydroxyimide or carboxy hydroxamic acid detergent additives of this invention.

The invention is further illustrated by the following examples, which should not be construed as limiting the scope of the invention.

EXAMPLE 1

A mixture of 10.78 g of hydroxylamine hydrochloride and 40 ml of methanol was heated in a 55° C. oil bath until a clear solution was obtained. The oil bath was removed and 35 ml of sodium methoxide solution (8.68 g sodium methoxide in 30 ml of methanol) was added to the solution. The mixture was stirred at room temperature for 30 minutes with occasional cooling in a water bath to maintain the temperature of the mixture below 35° C.

The mixture was then filtered, and to the filtrate cooled in an ice-salt bath was added 19.74 g of trimellitic anhydride. The mixture was stirred in the ice-salt bath for a few minutes, then warmed slowly to room temperature.

The anhydride was not soluble in the reaction mixture; however as the reaction proceeded, the reaction mixture turned to a clear solution. After stirring overnight a yellow wet cake was obtained.

Infrared (IR) spectroscopic analysis of the reaction mixture indicated that reaction with the hydroxylamine had taken place. High pressure liquid chromatography (HPLC) indicated that most of the product was cyclic N-hydroxyimide.

The reaction mixture containing the product was filtered. The solid collected was washed with methanol and vacuum dried; 12.5 g of dried solid was obtained.

EXAMPLE 2

To 300 ml of a 50% aqueous 4-sulfophthalic anhydride solution was added 24.43 g of NaOH. The mixture turned to a dark red solution after a few minutes. The solution was then stripped of water in a rotary evaporator, and 200.2 g of a light pink solid residue were obtained after vacuum drying at 60° C.

The light pink solid product was then heated in a vacuum oven at 150° C. for 7 hours. IR analysis indicated that the solid had been converted to 4-sulfophthalic anhydride. A mixture of 280 ml of methanol and 41.8 g of hydroxylamine hydrochloride was heated in a 60° C. oil bath until the hydroxylamine salt was dissolved. The oil bath was removed and 153 ml of a methanol solution (containing 33.5 g sodium methoxide) were added. The mixture was stirred at room temperature for 15 minutes, then stirred in an ice water bath for 15 minutes, and then filtered.

The filtrate was cooled in an ice water bath and 100 g of the synthesized 4-sulfophthalic anhydride was added. The reaction mixture was stirred overnight, and the ice water bath was allowed to warm to room temperature.

A dark orange solution containing some solid was obtained. The mixture was filtered, and about 10 g of white solid were collected.

The filtrate was then concentrated to about 350 ml and an equal amount of anhydrous diethyl ether was added. A large amount of precipitate appeared. The precipitate was collected by filtration and then vacuum dried at 80° C. About 55 g of N-hydroxyimide (most of it in the unopened form) was obtained.

EXAMPLE 3

The performance of the N-hydroxyimide compound of Example 1 as a fabric-washing detergent additive was examined in a tea stain removal test:

Swatches of white cotton cloth were boiled in very strong tea (10 tea bags/1 liter dionized water, brewed 10 min.) for 15 minutes. The tea solution and swatches were removed from the heat and cooled to 115° F. with stirring. The swatches were thereafter wrung and air dried between paper towels.

Dionized water was heated to 40° C. and 0.1 g of $CaCl_2$ were added per each liter of water, followed by 1.5 g per liter of water of a commercial fabric-washing detergent (Tide®; Procter & Gamble).

To 1-liter aliquots of this detergent solution were added 100 mg of the detergent additives to be tested, which were stirred until dissolved. The wash solutions were maintained at about 35° C. and a stirring speed of 100 rpm. The pH was adjusted to 10 if necessary with sulfuric acid or sodium hydroxide. Tea stained swatches of cloth were added to each test solution and stirred rapidly for 10 minutes, after which the solution was poured off and the swatches squeezed out and rinsed for 2 minutes in dionized water containing the same proportion of $CaC_2$. The swatches were then air dried overnight and compared against a control solution.

A sample of the compound of Example 1 was tested and showed very good tea stain removal capability when compared with a control detergent solution in which no detergent additive was used.

It will be understood that the foregoing description of the invention is susceptible to modifications, changes and adaptations, all of which are intended to be comprehended within the meaning and range of equivalents of the appended claims. For instance, though the foregoing description is directed to the use of the N-hydroxyimides in detergent systems, they will also find application in boiler water systems and other scale prevention uses, polymerization intermediates, and other embodiments where strong metal ion chelation is required.

We claim:

1. A detergent composition comprising an effective amount of one or more detersive surfactants and an effective amount of one or more chelating agents consisting essentially of substituted N-hydroxyimide compounds having the formula

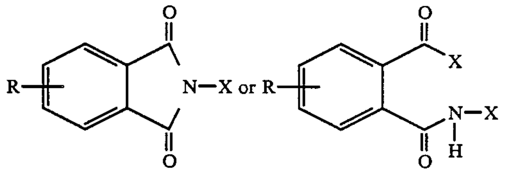

wherein R is carboxy, sulfo, $C_1$–$C_{12}$ carboxyalkyl or sulfoalkyl, or alkali metal salts of any of the foregoing, and X is —OH or —$O^-M^+$, where $M^+$ is an alkali metal cation.

2. A detergent composition according to claim 1 wherein said substituted N-hyroxyimide compound is selected from the group consisting of N-hydroxy-5-carboxy-phthalimide, N-hydroxy-5-sulfo-phthalimide, 1,4-dicarboxy-2-hydroxamobenzene, 1-hydroxamo-2, 4-carboxy-benzene, 1-carboxy-2-hydroxamo-4-sulfo-benzene, 1-hydroxamo-2-carboxy-4-sulfobenzene, alkali metal salts thereof, and mixtures thereof.

3. A detergent composition according to claim 1, wherein said detersive surfactant is an anionic surfactant, a non-ionic synthetic surfactant, or a combination of anionic and non-ionic surfactants.

4. A detergent composition according to claim 1, wherein the detersive surfactant is a soap or mixture of soaps.

5. A detergent composition according to claim 1, wherein the detersive surfactant is a non-ionic synthetic surfactant, or a combination of non-ionic synthetic surfactants.

6. A detergent composition according to claim 1 in the form of a concentrated aqueous solution having a pH of at least 9.

7. A detergent composition according to claim 1, which-further includes lather boosters, fillers, antiredeposition agents, fluorescers, pigments, germicides, scents, enzymes, or conventional detergent builders.

8. A detergent composition comprising one or more detersive surfactants comprising about 1% to 50% by weight of the total composition and one or more substituted N-hydroxyimide compounds having the formula

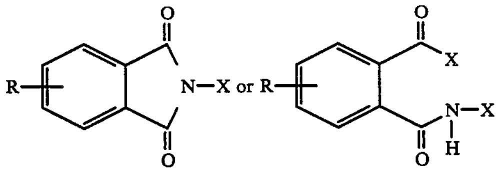

wherein R is carboxy, sulfo, $C_1$-$C_{12}$ carboxyalkyl or sulfoalkyl, or alkali metal salts of any of the foregoing, and X is —OH or $—O^-M^+$, where $M^+$ is an alkali metal cation, said substituted N-hydroxyimide compounds comprising about 3% to 12% by weight of the total composition.

9. A detergent composition according to claim 7, wherein the combined detergent builders comprise from about 10% to 50% by weight of the total detergent composition.

* * * * *